United States Patent [19]

Theodoropulos

[11] Patent Number: 5,220,000

[45] Date of Patent: Jun. 15, 1993

[54] BIFUNCTIONAL-BIS-QUINOLINOLS, AND THEIR METAL CHELATES

[76] Inventor: Spyros Theodoropulos, 2964 Hickory St., Yorktown Heights, N.Y. 10598

[21] Appl. No.: 824,300

[22] Filed: Jan. 23, 1992

[51] Int. Cl.[5] .................. C07D 215/16; C07D 215/20; C07F 13/00; C07F 5/00

[52] U.S. Cl. ........................................ 534/14; 534/15; 546/7; 546/8; 546/155; 558/17; 560/358; 564/372

[58] Field of Search ...................... 546/8, 155; 534/14, 534/15; 564/372; 560/358; 558/17

[56] References Cited

U.S. PATENT DOCUMENTS 4,152,401 5/1979 Langer, Jr. et al. .................... 546/8

*Primary Examiner*—Floyd D. Higel

[57] ABSTRACT

Novel bifunctional bis-quinolinols are provided as well as their chelates and processes for their production. The quinolinols can be attached to organic substrates before or after chelation and are useful for diagnostic and therapeutic purposes.

13 Claims, No Drawings

BIFUNCTIONAL-BIS-QUINOLINOLS, AND THEIR METAL CHELATES

BACKGROUND OF THE INVENTION

1) Field of the Invention

This invention relates to novel bifunctional chelating agents derived from 4,8-dihydroxyquinoline-2-carboxylic acid, useful in radioisotopic labeling of organic substrates. In one aspect this invention relates to chelating agents which have the ability to react with compounds of biological or clinical interest to form derivatives which will chelate suitable radionuclides, resulting in radioisotopic labeling of the compounds. The bis-quinolinol chelates of the invention are particularly useful as imaging agents for investigating organ functions in warm blooded animals, and for localizing radioactivity for diagnostic or therapeutic purpose.

2) Description of the Related Art

It is known that chelating agents such as ethylenediaminetetraacetic acid dianhydride (EDTA-dianhydride) or diethylenetriaminepentaacetic acid dianhydride (DTPA dianhydride) can be directly coupled to biological substrates to form conjugates which can be labeled with radionuclides used in in vivo imaging applications. However, EDTA and DTPA conjugates have shown limitations as to the variety of radionuclides that can be chelated, and as to their in vivo stabilities.

Accordingly, one or more of the following objects will be achieved by the practice of the present invention. It is an object of this invention to provide bis-quinolinols which are capable of forming chelates with a variety of radionuclides. Another object of this invention is to provide bifunctional bis-quinolinols which can be readily coupled to biological substrates, and the conjugates so formed can then be labeled with radionuclides which are suitable for diagnosis and therapy. It is a further object of the invention to provide radioisotope labeled compounds possessing superior in vivo stabilities. These and other objects will readily become apparent to those skilled in the art in the light of the teachings herein set forth.

SUMMARY OF THE INVENTION

In its broad aspect, this invention is directed to bifunctional chelating agents characterized by the structural formula:

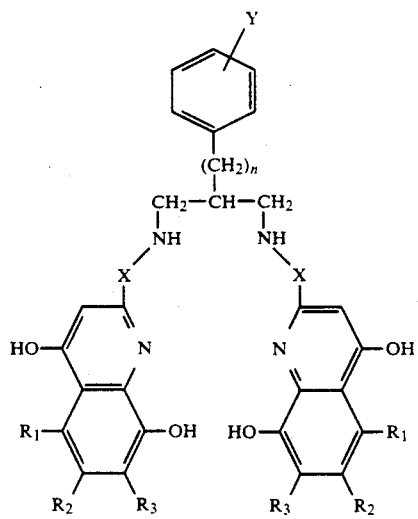

wherein n is 1 to 5; x is $CH_2$ or $-C=O$; y is $NO_2$, $NH_2$, $-N=C=S$, $-N=C=O$, $N_3$, $-NH-CO-NHNH_2$, $-NH-C(=S)-NHNH_2$, maleimido, $-NH-C(=S)-NH-$alkyl or $-NH-C(=S)-NH-$aryl. The term "alkyl" in the above y group is meant to include substituted alkyl groups from up to 18 carbon atoms containing carboxylic group such as carboxymethyl, carboxyethyl, carboxypropyl, and the like. The term "aryl" in the above y group is meant to include groups such as carboxyphenyl, dicarboxyphenyl, and the like. $R_1$, $R_2$ and $R_3$ can individually be the same or different and can represent hydrogen, COOH, $NO_2$, NO, $SO_3H$, halogen, $PO_3H$, an azo group, $NH_2$, alkyl, or aryl group; the term "alkyl" in the R groups is C-1 to C-12, saturated or unsaturated, which may be substituted; the term "aryl" in the R groups is meant to include aromatic groups from up to 18 carbon atoms, and which may be substituted.

The bifunctional bis-quinolinols of the invention contain, in addition to the chelating groups, a moiety which allows for the coupling of the chelating agent to organic compounds of interest. The resulting conjugates can then be readily chelated with radionuclides; the resultant radiolabeled conjugates can be used to localize radioactivity in specific organs in vivo, for diagnostic or therapeutic applications.

DETAILED DESCRIPTION OF THE INVENTION

The bifunctional bis-quinolinols of the present invention have the following formula:

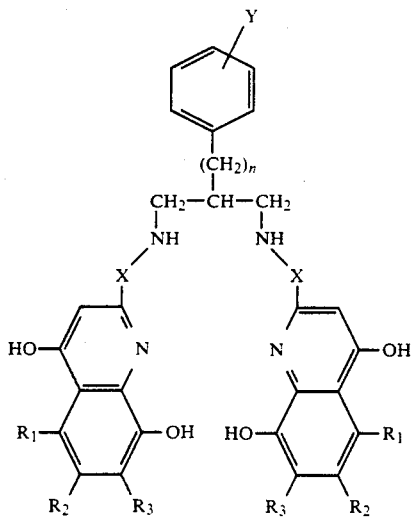

wherein n is 1 to 5; x is $CH_2$ or $-C=O$; y is $NO_2$, $NH_2$, $-N=C=S$, $-N=C=O$, $N_3$, $-NH-CO-NHNH_2$, $-NH-C(=S)-NHNH_2$, maleimido, $-NH-C(=S)-NH-alkyl$ or $-NH-C(=S)-NH-aryl$. The term "alkyl" in the y group is meant to include substituted alkyl groups from up to 18 carbon atoms containing carboxylic group such as carboxymethyl, carboxyethyl, carboxypropyl, and the like. The term "aryl" in the y group is meant to include groups such as carboxyphenyl, dicarboxyphenyl, and the like. $R_1$, $R_2$ and $R_3$ individually can be the same or different and represent hydrogen, COOH, NO, NO, SOH, halogen, POH, an azo group, $NH_2$, alkyl, or aryl group; the term "alkyl" in the R groups is C-1 to C-12, saturated or unsaturated, which may be substituted; the term "aryl" in the R groups is meant to include aromatic groups from up to 18 carbon atoms, and which may be substituted. are the same as $R_1$.

The bis-quinolinols of the present invention were synthesized using conventional techniques, and employing either readily available materials or reagents specially designed for this purpose. A preferred method for preparing the bis-quinolinols of this invention is to react a diamine of the formula I

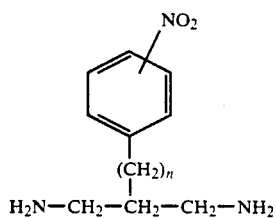

wherein n is as indicated above, with 4,8-dihydroxyquinoline-2-carboxylic acid succinate ester of the formula:

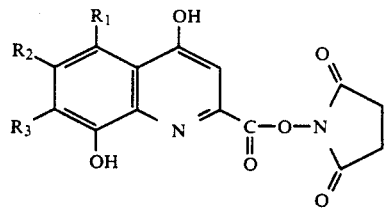

wherein $R_1$, $R_2$ and $R_3$ are as indicated above.

The bifunctional bis-quinolinols are conveniently prepared by reaction of the above compounds in an inert organic solvent at a temperature and for a period of time sufficient to form the desired polymers. The solvents which may be employed include tetrahydrofuran, toluene, dimethylformamide, methylene chloride, ethylacetate, dimethylsulfoxide, ethers, dioxane, and the like. The temperature of the reaction ranges from 0° to 100° C., with ambient temperature preferable.

An alternative method is to react the diamine I, indicated above, with 4,8-dihydroxyquinoline-2-carboxylic acid in an appropriate inert solvent in the presence of a dehydrating agent. The solvents which may be employed are the same as in the first method. The dehydrating agents which may be employed are carbodiimides, phosphorusoxychloride, or thionylchloride, with dicyclohexylcarbodiimide being the preferred agent. The temperature of the reaction ranges from 0° to 100° C., with ambient temperature being preferable.

The diamines of the formula I have been either obtained from commercial sources or specifically synthesized for this purpose. The following examples illustrate the methods applied for the synthesis of the diamines and the bifunctional chelating agents. Examples 1 through 3 describe the synthesis of the diamine I. Examples 4 through 6 describe the synthesis of the bis-quinolinols.

The bifunctional bis-quinolinols of this invention can be coupled to biological substrates or clinical compounds of interest, through the Y moiety in various ways, to form adducts. For example, when the Y moiety is an amine group, coupling may occur through carboxylic groups of the protein, especially from aspartic acid or glutamic acid residue on the protein. When the Y moiety is isothiocyanate, coupling may occur readily, via thiourea linkage, with proteins and other biological substrates possessing an amine group with an active hydrogen. When the Y moiety is maleimido group, coupling may occur with sulfhydryl groups of proteins or other molecules. When the Y moiety is an amine group, coupling to substrates of interest may occur with the aid of bifunctional coupling agents. A variety of coupling agents are now commercially available, and the method of coupling utilizing these reagents is very well known. The addition of the bifunctional bis-quinolinols of this invention and biological substrates can be represented by the formula:

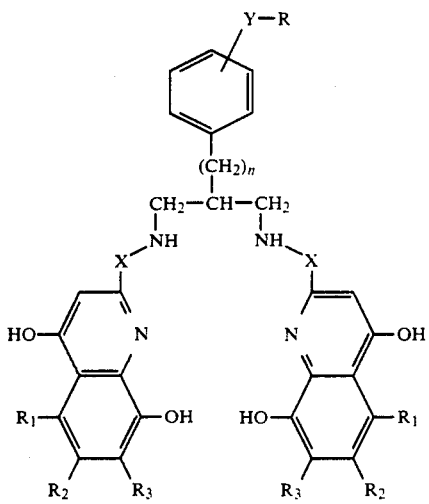

wherein n, x, y and the R1, R2 and R3 groups are as previously indicated, and R is the residue of an organic biological substrate to which the bisquinolinol moiety is attached.

The bis-quinolinols or the bis-quinolinol adducts of this invention are receptive to chelation. The choice of the particular radionuclide will, of course, be dependent on the intended use of the chelate (whether diagnosis or therapy), and on the ability of the particular radionuclide to complex with the chelating agent. Illustrative are: technitium-99m or indium-111 for diagnosis, and yttrium-90, rhenium-188 or holmium-166 for therapy.

While not wishing to be bound by a specific configuration as to the binding sites, the structure of the chelates can be depicted as follows:

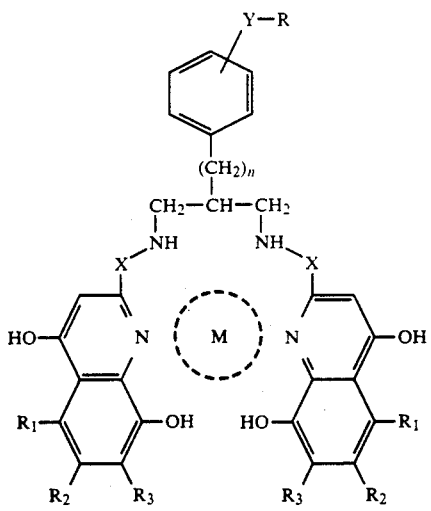

wherein M represents the transition metal ion and the remaining substituents are as previously indicated.

In practice, the chelates are formed by reacting the quinoline derivatives with a salt of the metal ion under conditions which promote the formation of a couple between the two reactants. A wide variety of metal salts of the metal ions can be utilized in the practice of the invention. The only requirement being that the metal salt is one which will form the metal chelate with the quinoline and will not adversely effect the properties of the final chelated compound. invention also encompass block and random copolymers, The choice of the particular metal ion will be dependent, of course, on the intended use of the chelate and whether such use is in vivo or in vitro, as well as the ability of the particular metal ion to form the chelate compound with the quinoline derivative.

Suitable ions, include but are not limited to, transition metal ions which are readioactive or paramagnetic and include radioactive metal ions such as, technetion-99m, indium-111, ytrium-90, gallium-67, osmium-67, cesium-137, and the like, and paramagnetic metal ions, such as, gondolinium, ferric ions, manganese, copper and the like. Thus for example, technetium-99 is preferred for radioisotopic imaging while ytrium-90 is preferred for radioisotopic therapy. Gondolinium is the preferred paramagnetic metal ion for use in nuclear magnetic resonance.

In practice, the chelates are formed by reacting the quinoline derivative with a salt of a metal ion by conventional procedures and under conditions which promote the formation of a complex between the two reactants. Salts which can be employed include, but are not limited to, the inorganic salts such as the chlorides, nitrates, sulfates and the like, and the organic salts such as metal alkoxy salts, triflates and the like.

As indicated above the preparation of the chelates of the quinoline derivatives and the metal ions is effected in the conventional manner. In practice this can be accomplished by contacting the quinoline derivative with the appropriate metal ion salt in an inert, liquid medium. As shown in the examples, the quinoline derivative and the metal salt were mixed in an inert liquid , such as methanol, and stirred at room temperature.

The chelated quinoline derivatives of this invention may be advantageously utilized in any of several known techniques involving the use of radioisotopes for diagnostic or therapeutic purposes, or in imaging systems which utilize nuclear magnetic resonance.

For example, the chelates of this invention can be employed in in vivo imaging to detect tumor cells or as diagnostic agents to determine the functioning of organs of warm blooded animals, including man. The particular chelate employed will be dependent upon the nature of the proposed diagnostic procedure or the intended therapeutic treatment. series.

The following examples illustrate the best mode presently contemplated for the preparation of bis-quinolinols, their adducts thereof, and the chelates:

EXAMPLE 1

4-Nitrobenzylidenemalononitrile

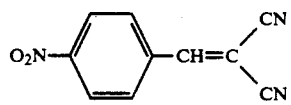

3.45 Grams(22.83 mmol) of 4-nitrobenzaldehyde and 1.52 grams(23.03 mmol) of malononitrile were dissolved in 200 milliliters of anhydrous ethanol. To this was added 0.35 milliliter of triethylamine, and the mixture was stirred and refluxed, under nitrogen, for 2 hours. The solvent was removed using a rotary evaporator and the crude reaction product was crystallized from ethanol. 2.33 Grams(51.5%) of the product was obtained. IR (in nujol) analysis showed bands at 3100, 3025, 2950–2850, 2220 (CN), 1595, 1570, 1510, 1450, 1410, 1365, 1340, 1315, 1300, 1210, 935, 850, 835, 780, 745, 680 and 620 cm$^{-1}$ NMR (CDCl$_3$) analysis showed signals at 8.40(d, 2H, J=9 Hz), 8.08(d, 2H, J=9 Hz) and 7.89(s, 1H) ppm.

EXAMPLE 2

Benzylmalononitrile

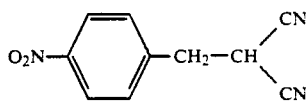

4.5 Grams of 4-nitrobenzylidenemalononitrile, prepared according to Example 1, was dissolved in 200 milliliters of ethylacetate. To this was added an aqueous solution of 0.54 gram of sodium borohydride in 5 milliliters of water, and the mixture was stirred at ambient temperature for ½ hour. The organic layer was separated, using a separatory funnel, and washed three times with water. The organic extract was dried over anhydrous sodium sulfate, and evaporated to dryness. The crude reaction product was crstallized from ethanol to obtain 3.07 grams(67.5% yield) of the product. IR(nujol) analysis showed bands at 3100, 2950–2850, 2250, 1980, 1595, 1505, 1450, 1440, 1370, 1340, 1290, 1175, 1100, 1010, 885, 860, 845, 755 and 710 cm$^{-1}$. NMR analysis (CDCl$_3$) showed signals at 8.30 (d, 2H, J=7.8 Hz), 7.56 (d, 2H, J=7.8 Hz), 4.05 (t, 1H, J=6.3 Hz) and 3.42 (d, 2H, J=6.3 Hz) ppm. Elemental analysis: C$_{10}$H$_7$N$_3$O$_2$ requires: C=59.7; H=3.48; N=20.90%. Found: C=59.62; H=3.39; N=20.81%.

EXAMPLE 3

1,3-Diamino-2-(4-nitrobenzyl)-propane

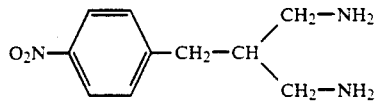

4-Nitrobenzylmalononitrile (2.48 g; 11.94 mmol) were dissolved in 30 mililiters of anhydrous tetrahydrofuran. The reaction mixture was stirred at ambient temperature for 24 hours, refluxed for one hour, and cooled to ambient temperature. To the reaction mixture were then added 50 milliliters of methanol followed by 40 milliliters of 6M hydrochloric acid. The reaction mixture was refluxed for 1.5 hours, cooled to room temperature, and concentrated on a rotary evaporator. The residual aqueous extract was made alkaline with 5M aqueous sodium hydroxide, and the product was thouroughly extracted with methylene chloride using a separatory funnel. Removal of methylene chloride on a rotary evaporator afforded 1.12 g of thick liquid product. TLC (silica gel; isopropanol/concentrated ammonium hydroxide/water 8:1:1): one spot, R$_f$=0.51. IR (neat) analysis showed bands at 3360, 3260, 2920, 2860, 1590, 1500, 1340, 1180, 1100, 1040, 850, 740, 700 cm$^{-1}$ NMR (DMSO-d$_6$+D$_2$O) analysis showed signals at 8.16 (dbr, 2H, J=8.1 Hz), 7.51 (dbr, 2H, J=8.1 Hz), 2.71 (d, 2H, J=7.2 Hz), 2.51 (d, 4H, J=5.4 Hz) and 1.72 (m, 1H) ppm.

EXAMPLE 4

1,3-Bis-(4,8-dihydroxy-2-carboxamido-quinolinyl)-2-(4-nitrobenzyl)-propane

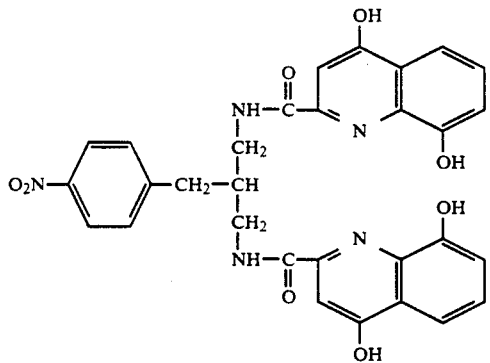

A mixture of 1.0 gram (4.88 mmol) of 4,8-dihydroxyquinoline-2-carboxylic acid, 0.62 gram (5.39 mmol) of N-hydroxysuccinimide and 1.10 grams (5.34 mmol) of dicyclohexylcarbodiimide in 10 milliliters of anhydrous dimethylformamide was stirred at ambient temperature for 6 hours under an inert atmosphere. To this was then added 0.62 gram(2.20 mmol) of 1,3-diamino-2-(4-nitrobenzyl)-propane dihydrochloride, made according to Example-3, followed by three milliliters of triethylamine. The mixture was stirred for 15 hours. The precipitated dicyclohexyl urea was filtered off, and the filtrate was evaporated to dryness under reduced pressure. The residual greenish gum was washed with water and triturated with methanol. The greenish yellow product was finally washed with methanol and diethyl ether and dried to obtain 0.47 gram of the product. High pressure liquid chromatography on Sperisorb ODS-2 (5 um particle size) analytical column, using 1;1 acetonitrile/water as solvent system, gave a peak with retention time at 2.39 minutes. TLC on 0.25 mm silica gel plate (EM Science) using 1;4 water/methanol as solvent system gave a single spot with R$_f$ of 0.32. NMR analysis (DMSO-d$_6$+D$_2$O) showed signals at 8.07 (dbr, 2H, J=8.1 Hz), 7.40–7.70 (complex multiplets, 8H), 7.16 (d, 2H, J=8.1 Hz), 3.50 (complex multiplets, 4H), 2.82 (complex multiplets, 2H) and 2.50 (multiplet, 1H) ppm.

EXAMPLE b 5

1,3-Bis-(4,8-dihydroxy-2-carboxamido-quinolinyl)-2-(4-aminobenzyl)-propane

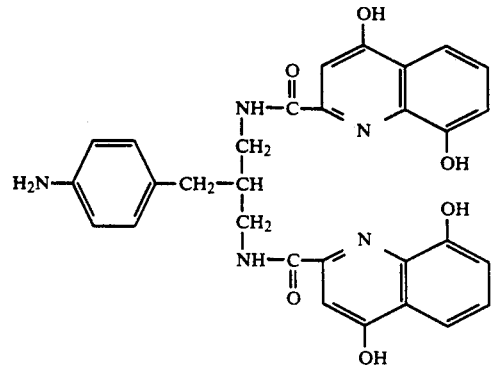

100 Milligrams of 1,3-bis-(4,8-dihydroxy-2-carbox-amido-quinolinyl)-2-(4-nitrobenzyl)-propane, made according to Example-4, was suspended in 100 milliliters of methanol. To this was added catalytic amounts of 10% Pd-C, and the mixture was subjected to pressure hydrogenation using 30 psi of hydrogen pressure. The catalyst was filtered off, and the filtrate was evaporated to dryness to obtain 95 milligrams of the product.

Although the invention has been illustrated by the preceding examples, it is not to be construed as being limited to the materials employed therein, but rather, the invention relates to the generic area as a whole. Various modifications and embodiments thereof can be made without departing from the spirit or scope thereof.

What is claimed is:

1. A compound of the formula:

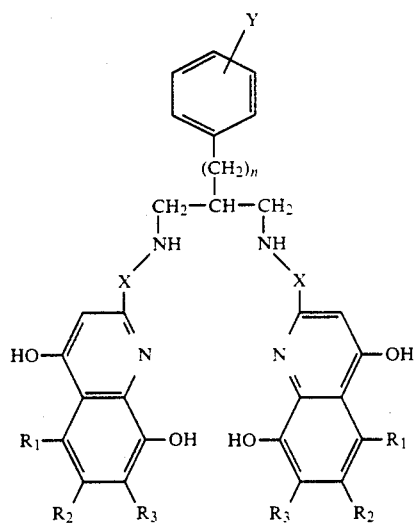

wherein n is 1 to 5; x is $CH_2$ or $-C=O$; Y is $NO_2$, $NH_2$, $-N=C=S$, $-N=C=O$, $N_3$, $-NH-CO-NHNH_2$, $-NH-C(=S)-NHNH_2$, maleimido, $-NH-C(=S)-NH-$alkyl or $-NH-C(=S)-NH-$aryl; wherewith term alkyl in y contains 1 to 18 carbon atoms and is an unsubstituted alkyl group or an alkyl group substituted with at least one carboxylic group, and the term hydrocarbon aryl in y contains 6 to 18 carbon atoms and is an unsubstituted hydrocarbon aryl group or an aryl group substituted with one or more carboxyl groups; $R_1$, $R_2$ and $R_3$ are hydrogen, COOH, $NO_2$, NO, $SO_3H$, halogen, $PO_3H$, an azo group, $NH_2$, alkyl, alkenyl or hydrocarbon aryl groups of from 1 to 18 carbon atoms and which may be substituted with one or more carboxyl groups.

2. A compound of the formula:

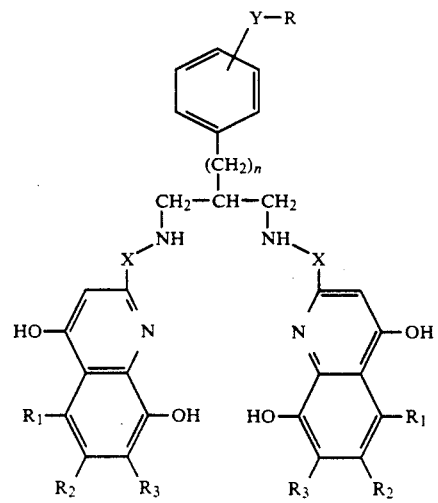

wherein R is an biological organic substrate and n, X, Y and $R_1$, $R_2$ and $R_3$ are as indicated in claim 1.

3. A compound of the formula:

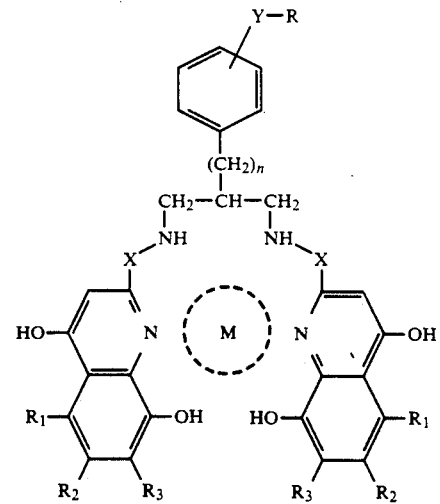

wherein M is a metal ion and n, X, Y and R, $R_1$, $R_2$ and $R_3$ are as indicted in claim 2.

4. A compound of the formula:

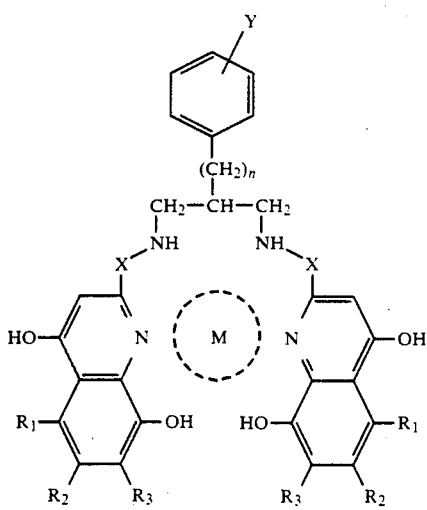

wherein M is a metal ion and n, X, Y and $R_1$, $R_2$ and $R_3$ are as indicted in claim 2.

5. A compound of the formula:

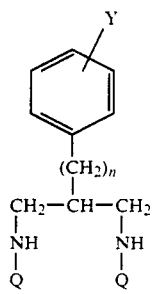

wherein n is 1 to 5; Y is $NO_2$, $NH_2$, NO, —N=C=S, —N=C=O, $N_3$, —NH—C(=S)—$NHNH_2$, —NH—CO—$NHNH_2$ or maleimido; and Q is a 4,8-dihydroxyquinolinyl group.

6. A compound of the formula:

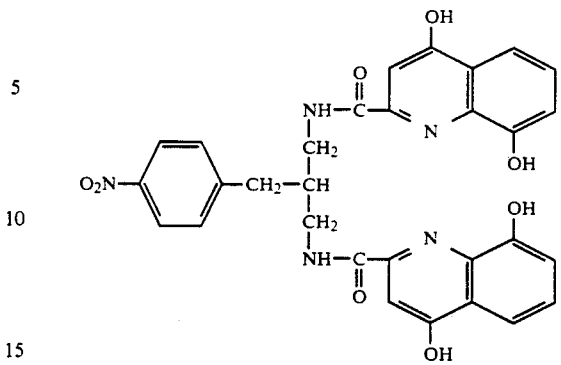

7. A compound of the formula:

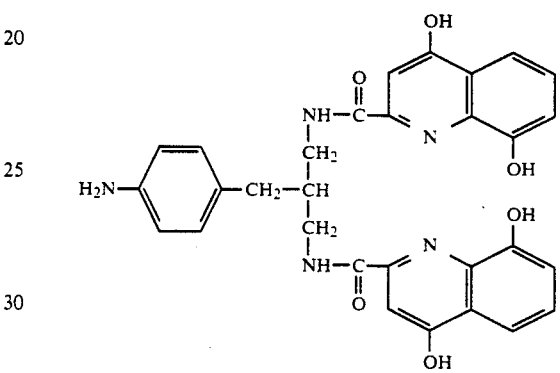

8. A chelate of a metal ion with the compound of claim 6.

9. A chelate of a metal ion with the compound of claim 7.

10. The compound of claim 6 which is attached to an biological organic substrate through the nitro group.

11. A chelate of a metal ion with the compound of claim 10.

12. The chelate of the compound of claim 11 wherein the metal ion is selected from the group consisting of technetium-99m, indium-111, yttrium-90, rhenium-188 and holmium.

13. The compound of claim 5 wherein Q is hydrogen.

* * * * *